(12) United States Patent
Nazzaro

(10) Patent No.: US 7,758,633 B2
(45) Date of Patent: Jul. 20, 2010

(54) VARIED DIAMETER VASCULAR GRAFT

(75) Inventor: Patrice Nazzaro, Hoboken, NJ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 960 days.

(21) Appl. No.: 10/823,456

(22) Filed: Apr. 12, 2004

(65) Prior Publication Data

US 2005/0228488 A1    Oct. 13, 2005

(51) Int. Cl.
*A61F 2/06* (2006.01)

(52) U.S. Cl. .................... 623/1.3; 623/1.51; 139/387 R

(58) Field of Classification Search ............. 623/1.3, 623/1.31, 1.2, 1.5, 23.64, 23.66, 23.7, 1.51, 623/1.1, 1.13; 606/108; 600/36; 139/384 R, 139/387 R See application file for complete search history.

(56) References Cited

U.S. PATENT DOCUMENTS

| | | | |
|---|---|---|---|
| 2,978,787 A | | 4/1961 | Liebig |
| 3,096,560 A | | 7/1963 | Liebig |
| 4,047,252 A | | 9/1977 | Liebig et al. |
| 4,193,137 A | | 3/1980 | Heck |
| 4,517,687 A | | 5/1985 | Liebig et al. |
| 4,530,113 A | | 7/1985 | Matterson |
| 4,695,280 A | | 9/1987 | Watanabe et al. |
| 4,743,250 A | | 5/1988 | Kitagawa et al. |
| 4,892,539 A | | 1/1990 | Koch |
| 4,969,896 A | | 11/1990 | Shors |
| 5,139,515 A | | 8/1992 | Robicsek |
| 5,178,630 A | | 1/1993 | Schmitt |
| 5,178,634 A | | 1/1993 | Martinez |
| 5,246,445 A | * | 9/1993 | Yachia et al. ............... 606/108 |
| 5,314,468 A | | 5/1994 | Martinez |
| 5,370,682 A | | 12/1994 | Schmitt |
| 5,383,925 A | | 1/1995 | Schmitt |
| 5,413,598 A | | 5/1995 | Moreland |

(Continued)

FOREIGN PATENT DOCUMENTS

WO    WO 9740755 A1  *  11/1997

*Primary Examiner*—Brian E. Pellegrino
(74) *Attorney, Agent, or Firm*—Vidas, Arrett & Steinkraus P.A.

(57) ABSTRACT

An implantable, varied-diameter graft is seamlessly flat-woven to provide a seamless, varied-diameter graft. The graft includes a flat-woven tubular portion having opposed first and second tubular ends with a contiguous bulbous woven section therebetween. The bulbous woven section has opposed first and second open ends with the first bulbous end being contiguous with the first tubular end. The second bulbous end is contiguous with the second tubular end. The first tubular end has a first number of warp yarns interlaced with a plurality of fill yarns in a woven pattern to define a first flat-woven tubular diameter. The second end has a second number of warp yarns interlaced with a plurality of fill yarns in a woven pattern to define a second flat-woven tubular diameter. The bulbous section has a third number of warp yarns interlaced with a plurality of fill yarns in a woven pattern to define a third flat-woven tubular diameter. The third number of warp yarns is greater than either of the first or said second number of warp yarns. Further, the third number of warps yarns are engagingly interlaced at the first bulbous end and disengagingly interlaced at second bulbous end to provide a seamless implantable graft having a third diameter being greater than either of said first or said second diameters.

10 Claims, 2 Drawing Sheets

U.S. PATENT DOCUMENTS

| | | |
|---|---|---|
| 5,445,599 A * | 8/1995 | Edenbaum .................... 602/76 |
| 5,628,786 A | 5/1997 | Banas et al. |
| 5,653,746 A | 8/1997 | Schmitt |
| 5,697,969 A | 12/1997 | Schmitt et al. |
| 5,741,332 A | 4/1998 | Schmitt |
| 5,769,884 A | 6/1998 | Solovay |
| 5,800,514 A | 9/1998 | Nunez et al. |
| 5,824,047 A | 10/1998 | Moreland |
| 5,843,158 A | 12/1998 | Lenker et al. |
| 5,861,026 A | 1/1999 | Harris et al. |
| 5,891,195 A | 4/1999 | Klostermeyer et al. |
| 5,904,714 A | 5/1999 | Nunez et al. |
| 5,913,894 A | 6/1999 | Schmitt |
| 6,090,137 A | 7/2000 | Schmitt |
| 6,136,022 A | 10/2000 | Nunez et al. |
| 6,176,875 B1 | 1/2001 | Lenker et al. |
| 6,193,754 B1 | 2/2001 | Seedhom |
| 6,342,070 B1 | 1/2002 | Nguyen-Thien-Nhon |
| 6,347,632 B1 | 2/2002 | Eberhardt et al. |
| 6,352,554 B2 | 3/2002 | DePaulis |
| 6,461,382 B1 | 10/2002 | Cao |
| 6,544,285 B1 | 4/2003 | Thubrikar et al. |
| 6,547,820 B1 | 4/2003 | Staudenmeier |
| 6,554,855 B1 | 4/2003 | Dong |
| 6,596,023 B1 | 7/2003 | Nunez et al. |
| 2003/0033008 A1 | 2/2003 | Schmitt et al. |
| 2003/0078650 A1 | 4/2003 | Nunez et al. |
| 2004/0019375 A1 | 1/2004 | Casey, II et al. |
| 2004/0049264 A1 | 3/2004 | Sowinski et al. |
| 2004/0093065 A1 * | 5/2004 | Yachia et al. .............. 623/1.13 |

* cited by examiner

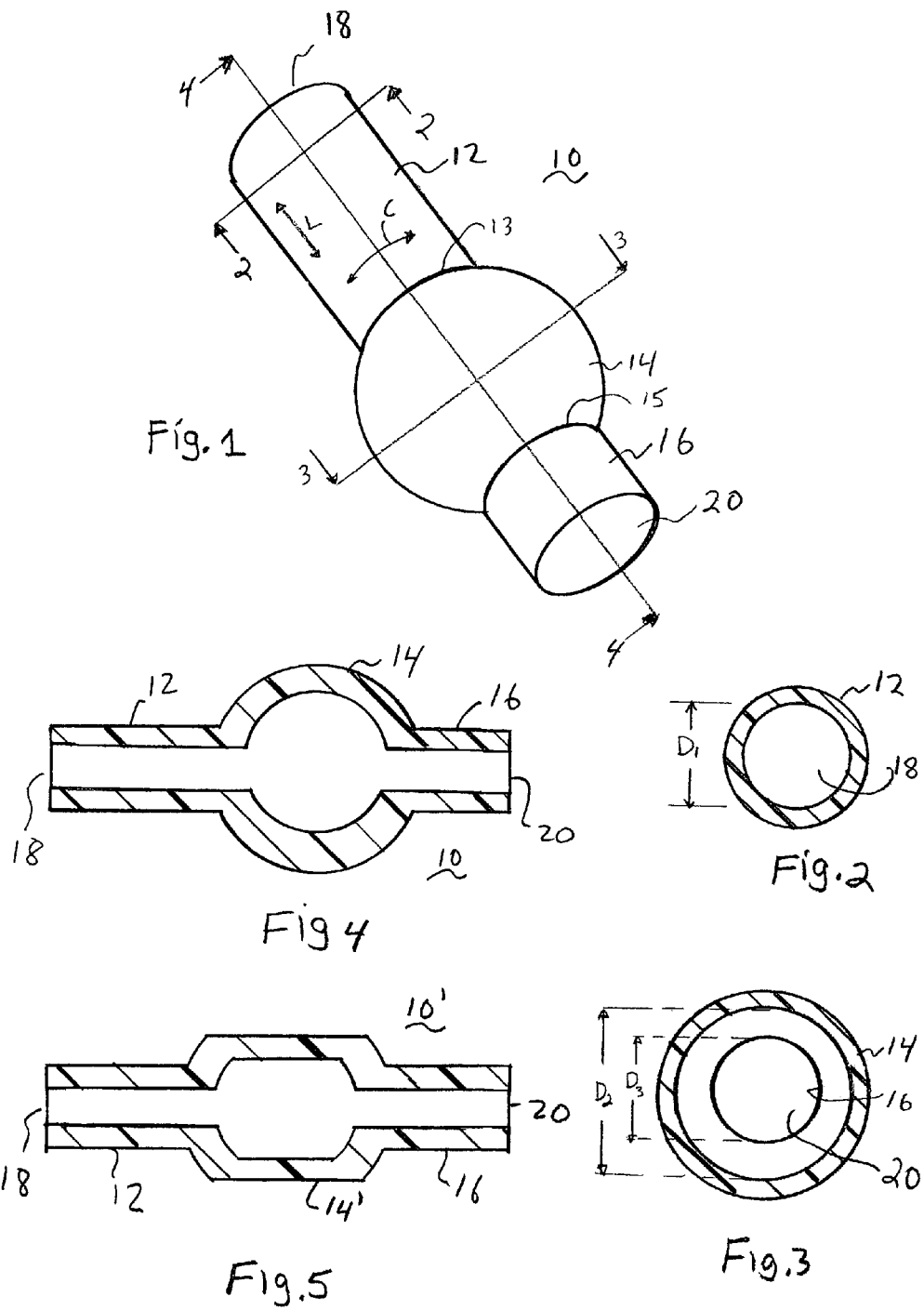

VARIED DIAMETER VASCULAR GRAFT

FIELD OF THE INVENTION

The present invention relates to varied diameter seamless woven tubular prostheses and methods of manufacture. In particular, the present invention relates to implantable endoluminal prostheses used in the vascular system.

BACKGROUND OF THE INVENTION

Tubular woven fabrics have been used for soft-tissue implantable prostheses to replace or repair damaged or diseased lumens in the body. In particular, endoprostheses are used in the vascular system to prevent the blood from rupturing a weakened section of the vessel. Such endoluminal conduits are generally affixed in a specified location in the vessel by means of stents, hooks or other mechanisms which serve to secure the device in place. Endoluminal tubular devices or conduits can also be used in other lumens in the body, such as in the esophagus and colon areas.

Weaving is commonly employed to fabricate various tubular shaped products. For example, implantable tubular prostheses which serve as conduits, such as vascular grafts, esophageal grafts and the like, are commonly manufactured using tubular weaving techniques, wherein the tubular product is woven as a flat tube. In such weaving processes, a variety of yarns are interwoven to create the tubular fabric. For example, a set of warp yarns is used which represents the width of the product being woven, and a fill yarn is woven between the warp yarns. The fill yarn is woven along the length of the warp yarns, with each successive pass of the fill yarn across the warp yarns for each side of the tube representing one machine pick. Thus, two machine picks represent one filling pick in a tubular woven structure, since weaving one fill yarn along the entire circumference of the tube, i.e., one filling pick, requires two picks of the weaving machine. As such, in a conventional woven product, the fill yarn is woven along the length of the warp yarns for a multiple number of machine picks, with the woven product produced defined in length by the number of filling picks of the fill yarn and defined in width by the number of warp yarns in which the fill yarn is woven therebetween.

Some damaged or diseased lumens, however, have quite complex shapes. For example, the root portion of the aorta is provided with sinuses or bulges that surround the aortic valve, which are called the sinuses of Valsalva. The diameter and orifice area of the aortic root are greater at the vicinity of the sinuses as compared to other portions of the root. With such a complex geometry, implantable grafts matching such complexity have often been made by suturing differently shaped graft components together. For example, U.S. Pat. No. 6,352,554 to DePaulis describes a method for forming a graft for the aortic root by suturing a bulbous woven section in between two straight tubular woven sections. Further, the bulbous woven section is also formed cutting or otherwise attaching woven materials. Such techniques are not only costly as numerous textile portions must be sutured to one and the other, but also serve as a potential source for leakage as it is difficult to suture fluid-tight seams among the textile components.

The present invention provides for a seamlessly woven varied diameter graft, such as but not limited to aortic root grafts, and methods for producing the same.

SUMMARY OF THE INVENTION

In one aspect of the present invention, an implantable graft is seamlessly flat woven with a varied diameter. The graft includes a flat-woven tubular portion having opposed first and second tubular ends with a contiguous bulbous woven section therebetween. The bulbous woven section has opposed first and second open ends with the first bulbous end being contiguous with the first tubular end. The second bulbous end is contiguous with the second tubular end. The first tubular end has a first number of warp yarns interlaced with a plurality of fill yarns in a woven pattern to define a first flat-woven tubular diameter. The second end has a second number of warp yarns interlaced with a plurality of fill yarns in a woven pattern to define a second flat-woven tubular diameter. The bulbous section has a third number of warp yarns interlaced with a plurality of fill yarns in a woven pattern to define a third flat-woven tubular diameter. The third number of warp yarns is greater than either of the first or the second number of warp yarns. Further, the third number of warps yarns are engagingly interlaced at the first bulbous end and disengagingly interlaced at second bulbous end to provide a seamless implantable graft having a third diameter being greater than either of the first or the second diameters.

The second number of warp yarns may be equal to the first number of warp yarns, which provides a graft with the second diameter being approximately equal to the first diameter. Desirably, the third diameter is from about 2 mm to about 20 mm greater that the first or the second diameter. The first diameter or the second diameter may vary from about 10 mm to about 50 mm.

The woven patterns of the first tubular end, the second tubular end and the bulbous section are selected from the group consisting a plain weave, a basket weave, a twill weave, a velour weave, a double velour weave, satin weave, terry weave and combinations thereof. The woven patterns of the first tubular end, the second tubular end and the bulbous section may be the same or may be different. Further, at least one of the woven portions of the first tubular end, the second tubular end and the bulbous section may have a different yarn density or may have the same yarn density. Moreover, at least one of the woven portions of the first tubular end, the second tubular end and the bulbous section may have a different yarn denier or may have the same yarn denier. Still further, at least one of the woven portions of the first tubular end, the second tubular end and the bulbous section may have a different yarn type or may be the same yarn type, where the different yarn type includes, but is not limited to of multifilament, monofilament, and staple. Additionally, at least one of the woven portions of the first tubular end, the second tubular end and the bulbous section may have a different yarn material or may have the same yarn material, where the different yarn material includes, but is not limited to, polyester, polypropylene, polyethylene, polyurethane, polytetrafluoroethylene and combinations thereof.

Desirably, the woven portions of the first tubular end, the second tubular end and the bulbous section are seamlessly transitioned.

Desirably, the warp yarns and the fill yarns are polymeric yarns, such as, but not limited to, of polyester, polypropylene, polyethylene, polyurethane, polytetrafluoroethylene and combinations thereof. Preferred warp and fill yarns include single ply, 70 denier, 54 filament, twisted flat polyester; double ply, 40 denier, 27 filament, twisted set polyester; or combinations thereof.

Further, the first bulbous end may include a textile portion having an increasing number of warp yarns at the rate of at least three or more warp yarns for every two of the fill yarns and a textile portion having a decreasing number of warp yarns at the rate of at least three warp yarns or greater for every two of the fill yarns. The bulbous section, which has opposed flat-woven edges, may be formed by threadingly engaging and disengaging the additional warp yarns at the opposed edges. Alternatively, the additional warp yarns may be threadingly engaged at different longitudinal locations along a length of the first bulbous end, and the additional warp yarns may be threadingly disengaged at different longitudinal locations along a length of the second bulbous end. Moreover, the additional warp yarns may be threadingly engaged at different radial locations along a width of the first bulbous end, and the additional warp yarns may be threadingly disengaged at different radial locations along a width of the second bulbous end.

The implantable graft of the present invention may be crimped, either totally or partially. For example, the tubular woven portion may be radially crimped. The bulbous woven portion may be radially crimped. The tubular and the bulbous woven portions may be radially crimped.

The implantable graft of the present invention may further include a mechanical or tissue heart valve securable attached to the second tubular end.

The implantable graft of the present invention may also be a multi-lumen structure, for example, the tubular end or the second tubular end may be a multi-lumen tubular structure.

In another aspect of the present invention, an implantable, flat-woven graft includes (i) a hollow tubular woven portion having opposed tubular ends and opposed flat-woven edges, the woven portion having a number of warp yarns interlaced with a number of fill yarns in a flat-woven tubular woven pattern to define a flat-woven tubular diameter; and (ii) a bulbous woven portion having a greater number of warp yarns interlaced with the fill yarns in a flat-woven tubular bulbous pattern contiguously woven between the opposed ends, wherein the greater number of warp yarns are threading engaged and disengaged with the fill yarns at different spaced-apart locations from the edges along the width of the graft at the bulbous woven portion to define a flat-woven bulbous diameter.

In yet another aspect of the present invention, an implantable graft includes a flat-woven tubular portion having opposed first and second tubular ends with a contiguous bulbous woven section therebetween, the bulbous woven section having opposed first and second open ends, the first bulbous end being contiguous with the first tubular end, the second bulbous end being contiguous with the second tubular end, the first tubular end having a first number of polymeric warp yarns interlaced with a plurality of polymeric fill yarns in a woven pattern to define a first flat-woven tubular diameter and a first woven length, the second end having a second number of polymeric warp yarns interlaced with the plurality of polymeric fill yarns in a woven pattern to define a second flat-woven tubular diameter and a second woven length, and the bulbous section having a third number of warp yarns interlaced with the plurality of fill yarns in a woven pattern to define a third flat-woven tubular diameter and a third woven length; where the third number of warp yarns is greater than either of the first or the second number of warp yarns to define an additional number of warp yarns; and further wherein the third number of warps yarns are engagingly interlaced at the rate of at least three or more warp yarns for every two of the fill yarns at the first bulbous end and disengagingly interlaced at the rate of greater than three warp yarns for every two of the fill yarns at second bulbous to provide a seamless implantable graft having a third diameter being greater than either of the first or the second diameters.

In a further aspect of the present invention, an implantable prosthesis includes (i) a first hollow tubular woven portion having a number of warp yarns interlaced with a first number of fill yarns in a flat-woven tubular woven pattern to define a flat-woven tubular diameter; (ii) a bulbous woven portion seamlessly transitioned from the first woven section, the bulbous woven section having a greater number of warp yarns interlaced with the fill yarns in a flat-woven tubular bulbous pattern; and (iii) a third hollow tubular woven portion seamlessly transitioned from the bulbous portion, the third woven portion having a third number of warp yarns interlaced with the number of fill yarns in a flat-woven tubular woven pattern to define a third flat-woven tubular diameter, wherein the greater number of warp yarns in the bulbous section is greater than the first or the third number of warp yarns.

A method for weaving the graft of the present invention includes the steps of (i) weaving a first flat-woven tubular section having opposed open ends and having a number of warp yarns and a number of fill yarns interlaced in a woven pattern to define a first flat-woven diameter; (ii) providing additional warp yarns; (iii) weaving the additional warp yarns into the woven pattern with the number of fill yarns at one of the open ends of the first tubular section to define a segment having a second flat-woven diameter, the second diameter being greater than the first diameter; and (iv) removing the additional warp yarns from the weaving pattern to provide a third woven section having a third diameter, where the third diameter is less than the second diameter.

BRIEF DESCRIPTION OF THE DRAWINGS

FIG. 1 is a perspective view of a varied diameter graft of the present invention having a bulbous portion.

FIG. 2 is a cross-sectional view off the graft of FIG. 1 taken along the 2-2 axis.

FIG. 3 is a cross-sectional view off the graft of FIG. 1 taken along the 3-3 axis.

FIG. 4 is a cross-sectional view off the graft of FIG. 1 taken along the 4-4 axis.

FIG. 5 is a cross-sectional view of the graft of the present invention depicting an alternate shape for the varied diameter graft of FIG. 1.

DETAILED DESCRIPTION OF THE PREFERRED EMBODIMENT

Figure 6:
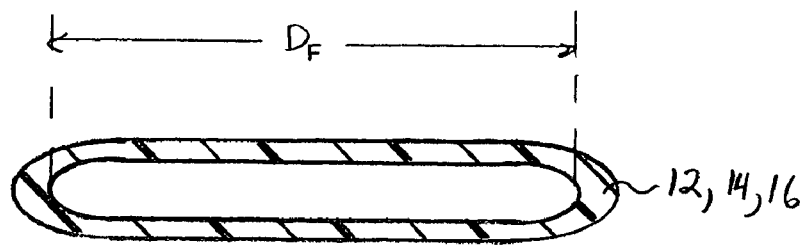
FIG. 6 is a cross-sectional view of a wall portion of the graft of the present invention depicting its flat-woven shape.

It has been discovered through the present invention that tubular woven textile products such as vascular grafts can be seamlessly woven into a variety of complex, varied-diameter shapes and sizes, without the need for any post-weaving fabrication techniques such as cutting, sewing, suturing and the like. One method for seamlessly weaving shaped tubular grafts is disclosed in U.S. Pat. No. 5,800,514 to Nunez et al., the contents of which are incorporated herein by reference. This patent describes shaped woven tubular grafts having a gradual woven transition between different sized or shaped tubular graft portions. For the more complex shaped grafts of the present invention such a gradual woven transition, however, may not result in a seamless graft which anatomically matches complex lumen contours, such as the aortic root.

FIG. 1 depicts a complex, varied-diameter graft 10 of the present invention. Graft 10 is suitable for replacement of the aortic root, but the present invention is not so limited. Graft 10 includes a first woven tubular section, a varied diameter bulbous woven section and a third woven tubular section 16. Although tubular sections 12 and 14 are depicted as straight tubular sections, the present invention is not so limited. For example, woven sections 12 and 16 may also have a varied diameter, for example a tapered shape. In weaving graft 10 warp yarns extend along the longitudinal direction of graft 10, which is depicted by vector "L". Fill yarns extend circumferentially or radially as depicted by vector "C". Graft 10 is woven as a single structure, i.e., a flat-woven, seamless, varied-diameter graft.

As depicted in FIGS. 2-4, graft 10 is a hollow device with opposed open ends 18 and 20. Tubular section 12 has a diameter of $D_1$. Tubular section 16 has a diameter of $D_3$. The two diameters, i.e., $D_1$ and $D_3$, may be the same or may be different. The bulbous section 14 has a varying diameter with its largest diameter represented by $D_2$. The bulbous diameter $D_2$ is larger than the tubular diameters $D_1$ and $D_3$ of the tubular sections 12 and 16.

The bulbous section 14 is depicted as a generally spherical section in FIG. 1. The present invention, however, is not so limited, and the bulbous section may have other outwardly extending or flared configurations. For example, the bulbous shape may be oblong or even partially truncated as shown in FIG. 5.

Figure 7:
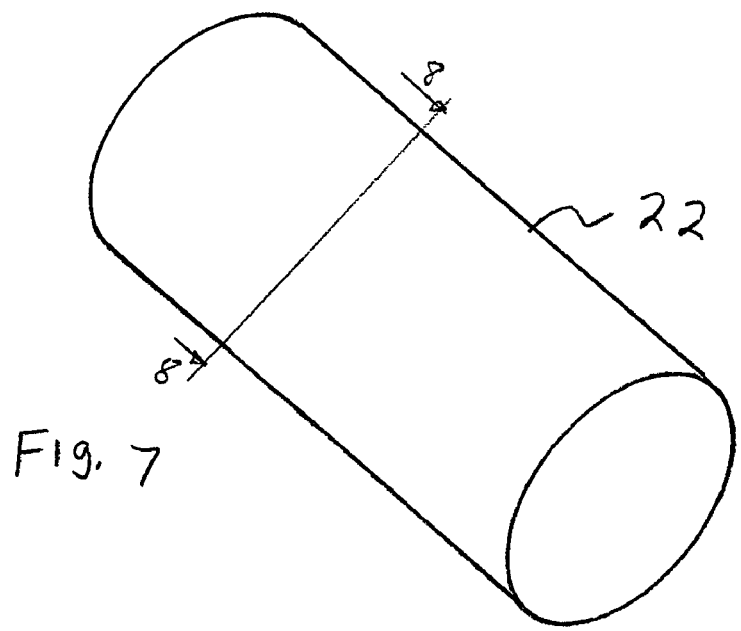
FIG. 7 is a perspective view of a mandrel useful for heat-setting portion of the graft of the present invention.
Figure 8:
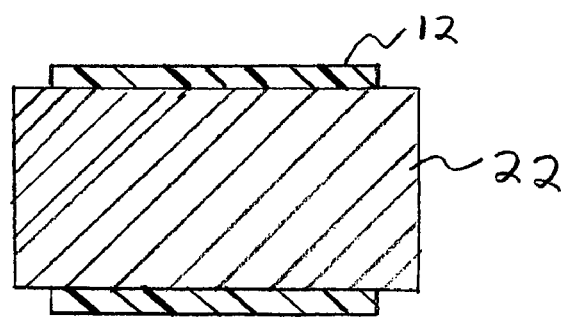
FIG. 8 is a cross-sectional view of a portion of the graft of the present invention disposed over the mandrel of FIG. 7.

The woven portions 12, 14, 16 of the present invention are flat-woven, tubular, seamless portions, as depicted in FIG. 6. Further, the transitions, such as portion 13 between woven sections 12 and 14, and portion 15 between woven portions 14 and 16, among the different woven sections are also seamlessly woven. The flat-woven diameter $D_F$ represents the width of the tubular fabric. To shape graft 10 into a three-dimensional device, portions of the graft or the entire graft may be heat set. An illustration of heat setting is depicted in FIGS. 7 and 8 for woven section 12. A tubular mandrel 22 is provided as depicted in FIG. 7. A portion of the graft 10, for example woven portion 12 is placed over the mandrel 22, typically by sliding. After heat-setting, which will be described below, the flat-woven portion is set into a three dimensional shape, for example, a hollow tubular shape as depicted in FIG. 1. The flat-woven diameter, $D_F$, thus represents about half of the circumference of the resulting heat-set tubular structure.

In one aspect of the present invention, an implantable graft is provided. The graft includes, but is not limited to, a flat-woven tubular portion having opposed first and second tubular ends with a contiguous bulbous woven section therebetween, the bulbous woven section having opposed first and second open ends, the first bulbous end being contiguous with the first tubular end, the second bulbous end being contiguous with the second tubular end, the first tubular end having a first number of warp yarns interlaced with a plurality of fill yarns in a woven pattern to define a first flat-woven tubular diameter, the second end having a second number of warp yarns interlaced with the plurality of fill yarns in a woven pattern to define a second flat-woven tubular diameter, and the bulbous section having a third number of warp yarns interlaced with the plurality of fill yarns in a woven pattern to define a third flat-woven tubular diameter; wherein the third number of warp yarns is greater than either of the first or the second number of warp yarns; and further wherein the third number of warps yarns are engagingly interlaced at the first bulbous end and disengagingly interlaced at second bulbous end to provide a seamless implantable graft having a third diameter being greater than either of the first or the second diameters.

The second number of warp yarns may be equal to the first number of warp yarns, which provides a graft with the second diameter being approximately equal to the first diameter. Desirably, the third diameter is from about 2 mm to about 20 mm greater that the first or the second diameter, more desirably from about 4 mm to about 12 mm, preferably about 8 mm. The first diameter or the second diameter may vary from about 10 mm to about 50 mm. Useful first and second diameters include, 24 mm, 26, mm, 28 mm, 30 mm and 32 mm. Preferred corresponding maximum diameters of the bulbous or sinus region include 32 mm, 34 mm, 36 mm, 38 mm and 40 mm. Desirably, the length of the bulbous section is at least equal to or greater than the diameter of the straight tubular portions, such as tubular portion 12.

The woven patterns of the first tubular end, the second tubular end and the bulbous section are selected from the group consisting a plain weave, a basket weave, a twill weave, a velour weave, a double velour weave, satin weave, terry weave and combinations thereof. The woven patterns of the first tubular end, the second tubular end and the bulbous section may be the same or may be different. Further, at least one of the woven portions of the first tubular end, the second tubular end and the bulbous section may have a different yarn density or may have the same yarn density. Moreover, at least one of the woven portions of the first tubular end, the second tubular end and the bulbous section may have a different yarn denier or may have the same yarn denier. Still further, at least one of the woven portions of the first tubular end, the second tubular end and the bulbous section may have a different yarn type or may be the same yarn type, where the different yarn type includes, but is not limited to of multifilament, monofilament, and staple. Additionally, at least one of the woven portions of the first tubular end, the second tubular end and the bulbous section may have a different yarn material or may have the same yarn material, where the different yarn material includes, but is not limited to, polyester, polypropylene, polyethylene, polyurethane, polytetrafluoroethylene and combinations thereof.

Desirably, the woven portions of the first tubular end, the second tubular end and the bulbous section are seamlessly transitioned.

Desirably, the warp yarns and the fill yarns are polymeric yarns, such as, but not limited to, of polyester, polypropylene, polyethylene, polyurethane, polytetrafluoroethylene and combinations thereof. Preferred warp and fill yarns include single ply, 70 denier, 54 filament, twisted flat polyester; double ply, 40 denier, 27 filament, twisted set polyester; or combinations thereof.

Further, the first bulbous end may include a textile portion having an increasing number of warp yarns at the rate of at least three or more warp yarns for every two of the fill yarns and a textile portion having a decreasing number of warp yarns at the rate of at least three warp yarns or greater for every two of the fill yarns. The bulbous section, which has opposed flat-woven edges, may be formed by threadingly engaging and disengaging the additional warp yarns at the opposed edges. Alternatively, the additional warp yarns may be threadingly engaged at different longitudinal locations along a length of the first bulbous end, and the additional warp yarns are threadingly disengaged at different longitudinal locations along a length of the second bulbous end. Moreover, the additional warp yarns may be threadingly engaged at different radial locations along a width of the first bulbous end, and the additional warp yarns may be threadingly disengaged at different radial locations along a width of the second bulbous end.

The implantable graft of the present invention may be crimped, either totally or partially. For example, the tubular woven portion may be radially crimped. The bulbous woven portion may be radially crimped. The tubular and the bulbous woven portions may be radially crimped.

The implantable graft of the present invention may further include a mechanical or tissue heart valve securable attached to the second tubular end.

The implantable graft of the present invention may also be a multi-lumen structure, for example the tubular end or the second tubular end may be a multi-lumen tubular structure.

In another aspect of the present invention, an implantable, flat-woven graft includes, but is not limited to, (i) a hollow tubular woven portion having opposed tubular ends and opposed flat-woven edges, the woven portion having a number of warp yarns interlaced with a number of fill yarns in a flat-woven tubular woven pattern to define a flat-woven tubular diameter; and (ii) a bulbous woven portion having a greater number of warp yarns interlaced with the fill yarns in a flat-woven tubular bulbous pattern contiguously woven between the opposed ends, wherein the greater number of warp yarns are threading engaged and disengaged with the fill yarns at different spaced-apart locations from the edges along the width of the graft at the bulbous woven portion to define a flat-woven bulbous diameter.

The implantable graft of the present invention may also include (i) a flat-woven tubular portion having opposed first and second tubular ends with a contiguous bulbous woven section therebetween, the bulbous woven section having opposed first and second open ends, the first bulbous end being contiguous with the first tubular end, the second bulbous end being contiguous with the second tubular end, the first tubular end having a first number of polymeric warp yarns interlaced with a plurality of polymeric fill yarns in a woven pattern to define a first flat-woven tubular diameter and a first woven length, the second end having a second number of polymeric warp yarns interlaced with the plurality of polymeric fill yarns in a woven pattern to define a second flat-woven tubular diameter and a second woven length, and the bulbous section having a third number of warp yarns interlaced with the plurality of fill yarns in a woven pattern to define a third flat-woven tubular diameter and a third woven length; wherein the third number of warp yarns is greater than either of the first or the second number of warp yarns to define an additional number of warp yarns; and further wherein the third number of warps yarns are engagingly interlaced at the rate of at least three or more warp yarns for every two of the fill yarns at the first bulbous end and disengagingly interlaced at the rate of greater than three warp yarns for every two of the fill yarns at second bulbous to provide a seamless implantable graft having a third diameter being greater than either of the first or the second diameters.

Still further, the implantable prosthesis of the present invention may include (i) a first hollow tubular woven portion having a number of warp yarns interlaced with a first number of fill yarns in a flat-woven tubular woven pattern to define a flat-woven tubular diameter; (ii) a bulbous woven portion seamlessly transitioned from the first woven section, the bulbous woven section having a greater number of warp yarns interlaced with the fill yarns in a flat-woven tubular bulbous pattern; and (iii) a third hollow tubular woven portion seamlessly transitioned from the bulbous portion, the third woven portion having a third number of warp yarns interlaced with the number of fill yarns in a flat-woven tubular woven pattern to define a third flat-woven tubular diameter, wherein the greater number of warp yarns in the bulbous section is greater than the first or the third number of warp yarns.

A method for weaving the graft according to the present invention includes the steps of (i) weaving a first flat-woven tubular section having opposed open ends and having a number of warp yarns and a number of fill yarns interlaced in a woven pattern to define a first flat-woven diameter; (ii) providing additional warp yarns; (iii) weaving the additional warp yarns into the woven pattern with the number of fill yarns at one of the open ends of the first tubular section to define a segment having a second flat-woven diameter, the second diameter being greater than the first diameter; and (iv) removing the additional warp yarns from the weaving pattern to provide a third woven section having a third diameter, where the third diameter is less than the second diameter.

The third number of warp yarns may be equal to the first number of warp yarns. Further, the third diameter may be equal to the first diameter. Desirably, the second diameter is from about 2 mm to about 20 mm greater that the first or the third diameter, wherein the first diameter or the third diameter is from about 10 mm to about 50 mm.

The woven patterns of the first tubular end, the second tubular end and the bulbous section may be selected from, but not limited to, a plain weave, a basket weave, a twill weave, a velour weave, a double velour weave, satin weave, terry weave, and combinations thereof. The woven patterns of the first tubular end, the second tubular end and the bulbous section may be the same or may be different.

Desirably, the warp yarns and the fill yarns are polymeric yarns, including materials such as polyester, polypropylene, polyethylene, polyurethane, polytetrafluoroethylene and combinations thereof. Preferably, the warp or fill yarns are single ply, 70 denier, 54 filament, twisted flat polyester; double ply, 40 denier, 27 filament, twisted set polyester; or combinations thereof.

Desirably, the step of weaving the additional warp yarns comprises increasing the number of warp yarns at a rate of greater than three warp yarns for every two of the fill yarns. Desirably, the step of removing the additional warp yarns comprises decreasing the number of warp yarns at a rate of greater than three warp yarns for every two of the fill yarns.

Any type of textile product can be used as the warp yarns and fill yarns of the present invention. Of particular usefulness in forming the woven prostheses of the present invention are synthetic materials such as thermoplastic polymers. Thermoplastic yarns suitable for use in the present invention include, but are not limited to, polyesters, polypropylenes, polyethylenes, polyurethanes and polytetrafluoroethylenes. The yarns may be of the monofilament, multifilament, or staple type.

The yarns used in forming the woven grafts of the present invention may be flat, twisted, textured or set, and may have high, low or moderate shrinkage properties. Additionally, the yarn type and yarn denier can be selected to meet specific properties desired for the prosthesis, such as porosity, flexibility and compliance. The yarn denier represents the linear density of the yarn (number of grams mass divided by 9,000 meters of length). Thus, a yarn with a small denier would correspond to a very fine yarn whereas a yarn with a larger denier, e.g., 1000, would correspond to a heavy yarn. The yarns used with the present invention may have a denier from about 20 to about 1000, preferably from about 40 to about 300. Preferably, the warp and fill yarns are polyester, and most preferably the warp and fill yarns are single ply, 70 denier, 54 filament, twisted flat polyester; double ply, 40 denier, 27 filament, twisted set polyester; or combinations thereof.

The graft of the present invention can be woven using any known weave pattern in the art, including, simple weaves, basket weaves, twill weaves, velour weaves and the like, and is preferably woven using a double velour tubular weave pattern. Details of double velour patterns are described in U.S. Pat. No. 4,517,687 to Liebig et al., the contents of which are incorporated by reference herein. Desirably, the double velour pattern includes a satin weave where a warp yarn crosses over or under at least four fill yarns. The weave patterns may have from about 50-200 warp yarns (ends) per inch per layer and about 30-100 fill yarns (picks) per inch per layer. The wall thickness of the graft may be any conventional useful thickness, for example from about 0.1 mm to about 1.20 mm, desirably from about 0.5 mm to about 0.9 mm.

Such a heat setting process is accomplished by first flat-weaving the graft in a tubular form out of a material capable of shrinking during a heat setting process. After the graft is woven, the graft is placed on a mandrel, and heated in an oven at a temperature and time capable of causing the yarns of the graft to heat set to the shape and diameter of the mandrel. Preferably polyester yarns are used as the warp and fill yarns, and the heat setting is accomplished at time and temperatures appropriate for the material. For example, heat setting can be accomplished at about 190-200° C. for a period of about 14-16 minutes. Other methods of heat setting may be employed, for example ultrasonic heat-setting, or through the use of steam as a heating source. One useful method of ultrasonic heat setting is described in U.S. patent application Ser. No. 10/822,955 titled "Ultrasonic Crimping Of A Varied Diameter Graft" and filed on Apr. 12, 2004, the contents of which are incorporated herein by reference. After heat setting, the graft can be formed into a shape desired for implantation.

The invention being thus described, it will now be evident to those skilled in the art that the same may be varied in many ways. Such variations are not to be regarded as a departure from the spirit and scope of the invention and all such modifications are intended to be included within the scope of the following claims. For example, the woven sections 14 or 16 may be provided with a scalloped or petaled shape for facilitating placement to a mechanical or human heart valve. Details of such shaping is further described in U.S. patent application Ser. No. 10/823,061 titled "Tri-Petal Aortic Root Vascular Graft"and filed on Apr. 12, 2004, the contents of which are incorporated herein by reference.

What is claimed is:

1. An implantable prosthesis comprising:
    a first hollow tubular woven portion having a number of warp yarns interlaced with a first number of fill yarns in a flat-woven tubular woven pattern to define a flat-woven tubular diameter;
    a generally spherical bulbous woven portion seamlessly transitioned from said first woven section, said bulbous woven section having a greater number of warp yarns interlaced with said fill yarns in a flat-woven tubular bulbous pattern, said bulbous woven portion including a first bulbous end and a second bulbous end, said first bulbous end including a textile portion having an increased number of warp yarns at the rate of more than three warp yarns for every two of said fill yarns, the second bulbous end including a textile portion having a decreasing number of warp yarns at the rate of at least three warp yarns or greater for every two of said fill yarns; and
    a third hollow tubular woven portion seamlessly transitioned from said bulbous portion, said third woven portion having a third number of warp yarns interlaced with said number of fill yarns in a flat-woven tubular pattern to define a third flat-woven tubular diameter, wherein said greater number of warp yarns of said bulbous portion is greater than said first or said third number of warp yarns;
    said woven pattern of said bulbous woven portion comprises a terry weave and said woven pattern of said first and third hollow tubular woven portions comprises a woven pattern selected from the group consisting of a plain weave, basket weave, twill weave, velour weave, double velour weave, satin weave, and combinations thereof.

2. The implantable prosthesis of claim 1, wherein said third number of warp yarns is equal to said number of warp yarns of said first woven portion.

3. The implantable prosthesis of claim 1, wherein said diameter of said third woven portion is equal to said diameter of said first woven portion.

4. The implantable prosthesis of claim 1, wherein said diameter of said first or said third woven portion is from about 10 mm to about 50 mm.

5. The implantable prosthesis of claim 1, wherein at least one of said first woven portion, said third woven portion, and said bulbous woven portion has a different yarn density.

6. The implantable prosthesis of claim 1, wherein at least one of said first woven portion, said third woven portion, and said bulbous woven portion has a different yarn denier.

7. The implantable prosthesis of claim 1, wherein at least one of said first woven portion, said third woven portion, and said bulbous woven portion has a different yarn material wherein the different yarn material is selected from the group consisting of polyester, polypropylene, polyethylene, polyurethane, polytetrafluoroethylene and combinations thereof.

8. The implantable prosthesis of claim 1, wherein said warp yarns and said fill yarns are polymeric yarns.

9. The implantable prosthesis of claim 1, wherein said warp yarns and said fill yarns include materials selected from the group consisting of polyester, polypropylene, polyethylene, polyurethane, polytetrafluoroethylene and combinations thereof.

10. The implantable prosthesis of claim 1, wherein said third number of warp yarns includes a varying number of warp yarns.

* * * * *